March 21, 1944. R. L. BYRUM Plant Pat. 620
ROSE PLANT
Filed Oct. 23, 1943
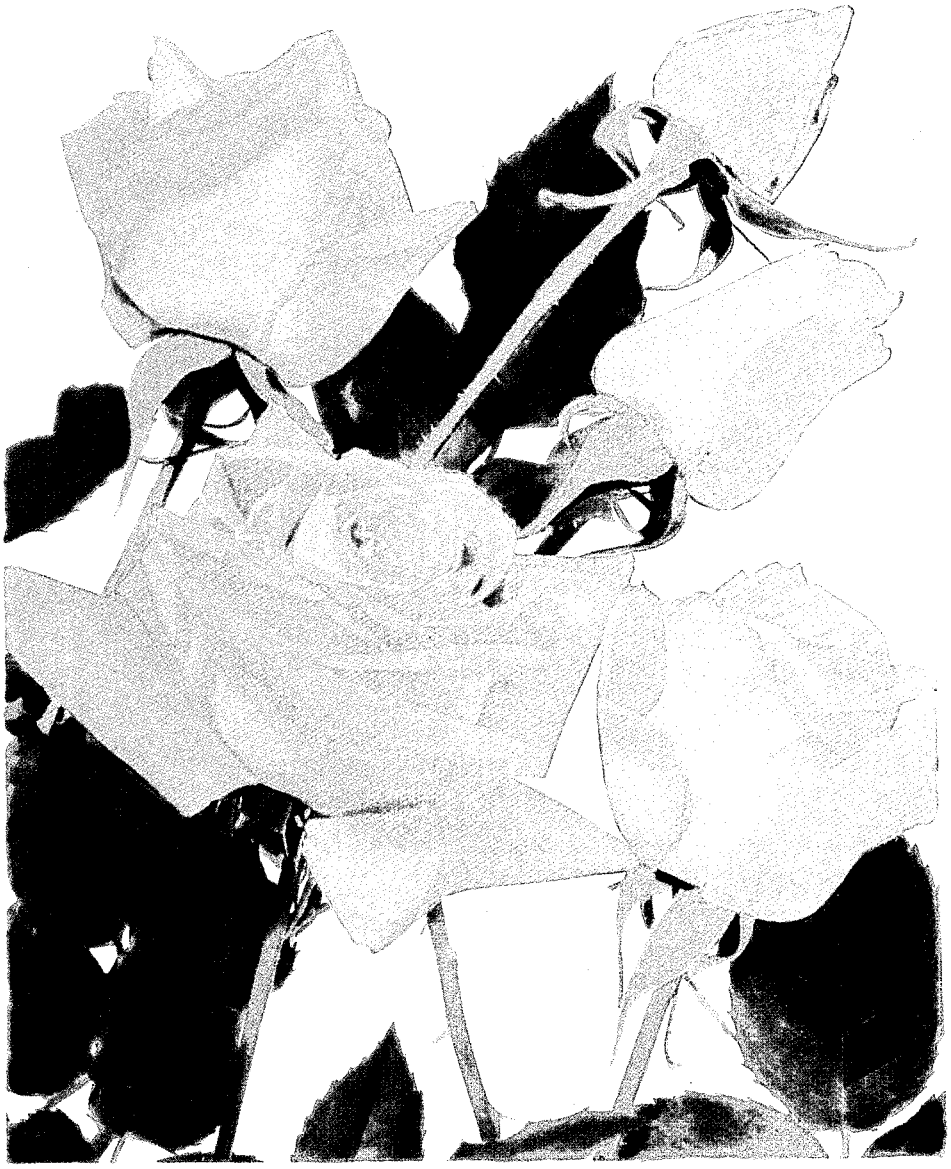
Inventor
Roy L. Byrum
By Robert Cobb
Attorneys Patented Mar. 21, 1944

Plant Pat. 620

UNITED STATES PATENT OFFICE

620

ROSE PLANT

Roy L. Byrum, Richmond, Ind., assignor to Joseph H. Hill Company, Richmond, Ind., a corporation of Indiana Application October 23, 1943, Serial No. 507,423

1 Claim. (Cl. 47—61)

The present invention relates to a new and distinct variety of rose plant of the hybrid tea class, originated by crossing the known varieties "Rome Glory" (Pl. Pat. #304) and "Chieftain" (Pl. Pat. #150).

The object in view was to obtain a new rose which would possess as many of the desirable characteristics of the parent varieties as possible with a general all around improvement in the progeny.

As a result of the cross, this new variety, while resembling its pollen parent in form, was found to possess the distinguishing characteristics of producing more blossoms per plant than either of its parents and blooms of more brilliant color than either. This color, in the newly opened rose, does not appear among Ridgway's color standards, and can, therefore, only be defined in general tonality as bright velvety Rose Red, toning down, after several days, to Rose Red of the Ridgway chart.

Another distinction of importance lies in the penetrating apple fragrance possessed by this new rose.

Other specific differences will become apparent from the following detailed description of this new variety, in which color terminology accords with Ridgeway's Color Standard, except where otherwise indicated to have ordinary dictionary significance:

Type: Half hardy; greenhouse; outdoor; seedling; for cut flowers and garden decoration.
Class: Hybrid tea.
Breeding: Seedling.
*Seed parent.*—"Rome Glory."
*Pollen parent.*—"Chieftain."
Propagation: Holds its distinguishing characteristics through succeeding propagations by grafting and budding.

*Flower*

Locality where grown: Richmond, Indiana.
Flowers borne: Singly to stem; irregular; on strong, medium long stems.
Quantity of bloom: Abundant in greenhouse.
Continuity: Continuous.
Fragrance: Penetrating; apple.
Bud:
*Peduncle.*—Medium long; medium heavy; medium erect; light green; entirely smooth; few green hairs and prickles.
*Before calyx breaks.*—
*Size* — medium. *Form* — short; pointed, with a conspicuous neck; without foliaceous appendages on the surface of the bud; with slender foliaceous parts extending beyond the tip of the bud equal to one-fourth of its length.
*As calyx breaks.*—*Color*—Carmine, Plate 1, overlaid with Ox Blood Red, Plate 1.
*As first petal opens.*—Size—large. *Form*—pointed; ovid. *Color*—outside—Rose Red, Plate 12, tinted with Tyrian Rose, Plate 12; inside—Rose Red, Plate 12, overlaid with very Bright Velvety Red (no corresponding color value found in Ridgway). *Opening*—Opens up well.
Bloom:
*Size.*—When fully open, very large; four inches to six inches.
*Petalage.*—Double; from thirty to thirty-five petals arranged irregularly.
*Form.*—Open; full; globular at first; becoming open; petals remaining at first tightly rolled outward; becoming later, at maturity, loosely rolled outward.
Petals: Thick; with inside velvety and outside shiny.
*Shape.*—Outside—obovate; scalloped with one notch. Intermediate—obovate. Inside—obovate; scalloped irregularly with one notch.

This description of a newly opened flowers was made from a rose grown in a greenhouse during the month of October, 1942, at Richmond, Indiana. (No corresponding color value in Ridgway for the Velvety Red color in open bloom):

*Color.*—*Outside petal*—outside surface — Rose Red, Plate 12, shading to Tyrian Rose, Plate 12; inside surface—Rose Red, Plate 12, overlaid with very Bright Velvety Red. Base of petal is Pale Lemon Yellow, Plate 4. *Intermediate petal*—outside surface—Rose Red, Plate 12, shading to Tyrian Rose, Plate 12; inside surface—Rose Red, Plate 12, overlaid with very Bright Velvety Red. Base of petal is Pale Lemon Yellow, Plate 4. *Inner petal*—outside surface—Rose Red, Plate 12, shading to Tyrian Rose, Plate 12; inside surface—Rose Red, Plate 12, overlaid with very Bright Velvety Red. Base of petal is Pale Lemon Yellow, Plate 4.

This description was made from a rose that was open for three days in a greenhouse, during the month of October, 1942, at Richmond, Indiana:

*Color.* — *outside petal* — outside surface — Rose Color, Plate 12, tinted with Tyrian Rose, Plate 12; base of petal—Picric Yellow, Plate 4; inside surface—Tyrian Rose, Plate 12, washed with Rose Red, Plate 12. *Inside petal*—outside surface—Rose Color, Plate 12, tinted with Tyrian Rose, Plate 12; base of petal—Picric Yellow, Plate 4; inside surface—Tyrian Rose, Plate 12, washed with Rose Red, Plate 12.
*General color effect.*—Newly opened flower—Bright Velvety Rose Red. Three days open—Rose Red, Plate 12.

*Behavior.*—Persist.
*Flower longevity.*—Cut roses grown in a greenhouse, kept at living-room temperatures, 5 to 7 days in October.

*Reproductive organs*

Stamens: Medium number; arranged regularly about pistils.
Filaments: Medium long; reddish; most with anthers.
Anthers: Small; Brown; all open at once.
Pollen: Very abundant; Gold.
Pistils: Many.
Styles: Uneven; medium length; thin; bunched.
Stigma: White.
Ovaries: Some protruding from calyx.
Sepals: Permanent; moderately long; spear-shaped; curled.
*Color.*—Inside — Biscay Green, Plate 17; white fuzz. Outside—Biscay Green, Plate 17.

*Plant*

Foliage:
*Leaves.*—Compound of five to seven leaflets; abundant; medium large; moderately heavy.
*Leaflets.*—*Shape*—ovoid with apex acute; base obtuse; margin simply serrate.
*Color.*—*Mature*—upper surface—very Dark Green; under surface—moderately Light Green.
*Rachis.* — Medium heavy. Upper side — grooved; hairy. Under side—moderately smooth; thorny.
*Stipules.*—Medium long; narrow; with medium long points, turning out at an angle of less than 45°.
*Disease.*—Resistant to mildew and blackspot insofar as this is evidenced by absence of any throughout development and establishing of this variety.
Growth:
*Habit.*—Bush; upright; much branched.
*Growth.*—Free.
*Canes.*—Medium heavy.
*Main Stems.*—Dull Green. *Thorns*—many; medium long; hooked downward; with round base. *Prickles* — few; Brown. *Hairs*—none.
*Branches.*—Green Bronze. *Thorns*—many; medium long; hooked downward; with long narrow base. *Prickles*—none. *Hairs*—many; reddish.
*New shoots.*—Bronze Red. *Thorns*—many; medium long; hooked downward; with long, narrow base. *Prickles*—several; reddish. *Hairs*—few; reddish.

I claim:

A new and distinct variety of Hybrid Tea Rose plant, characterized as to novelty by the prolificacy of blooming, the unusual coloring and fragrance of the flowers, and their lasting quality, substantially as shown and described.

ROY L. BYRUM.